United States Patent [19]
Edelstein

[11] Patent Number: 4,890,741
[45] Date of Patent: Jan. 2, 1990

[54] CAPSULE PACKAGE

[76] Inventor: Alan D. Edelstein, 41 Highland Ave., Winchester, Mass. 01890

[21] Appl. No.: 232,939

[22] Filed: Aug. 17, 1988

[51] Int. Cl.[4] .................. B65D 83/04; B65D 85/56
[52] U.S. Cl. .................................. 206/534; 206/232; 206/538; 220/23.83; 220/20
[58] Field of Search ............... 206/223, 232, 570, 581, 206/534, 538, 540, 828, 823, 822, 803, 370, 459; 220/23.83, 20, 22; 383/86

[56] References Cited
U.S. PATENT DOCUMENTS

| 303,958 | 8/1884 | Vaughan | 206/576 X |
|---|---|---|---|
| 1,648,565 | 11/1927 | Primley | 206/232 X |
| 3,389,784 | 6/1968 | Hendricks et al. | 206/803 |
| 3,638,603 | 2/1972 | Conover | 206/538 X |
| 3,780,856 | 12/1973 | Braverman . | |
| 3,981,402 | 9/1976 | Miller . | |
| 4,039,080 | 8/1977 | Cappuccilli . | |
| 4,211,329 | 7/1980 | Braverman . | |
| 4,286,639 | 9/1981 | Murphy | 383/86 X |
| 4,371,080 | 2/1983 | Haines . | |
| 4,461,332 | 7/1984 | Parkhurst | 206/823 |
| 4,553,670 | 11/1985 | Collens . | |
| 4,781,773 | 4/1988 | Instance | 206/822 X |

FOREIGN PATENT DOCUMENTS

| 859539 | 12/1970 | Canada . | |
|---|---|---|---|
| 1085877 | 8/1954 | France | 206/459 |
| 768914 | 2/1957 | United Kingdom . | |
| 792087 | 3/1958 | United Kingdom | 206/370 |

OTHER PUBLICATIONS

Thomas Moulding, Notes and Correspondence, American Review of Respiratory Diseases, 1961.
Thomas S. Moulding, M.D., "Varied Designs for Pill Calendars and Time Recording Pill Dispensers", Copyright 1965.

Primary Examiner—William Price
Attorney, Agent, or Firm—Charles Hieken

[57] ABSTRACT

A pair of receptacles are connected together by flexible material for permitting the receptacles to be assembled in overlapping relationship to form a convenient package. Each receptacle includes a medication storage compartment having a child-resistant cap assembly that is easily opened by a patient with malfunctioning fingers and a smaller, adjacent compartment for receiving the cap assembly of another receptacle. Large indicia with instructions for taking the medication stored in the medication storage compartment may be inserted into this smaller compartment.

20 Claims, 5 Drawing Sheets

CAPSULE PACKAGE

BACKGROUND OF THE INVENTION

This invention relates to a medication dispensing system that includes a plurality of interconnecting receptacles for storing, dispensing, transporting and identifying medication with indicia prominently displaying instructions for taking the medication within each receptacle This system would provide a summary of the medications and associated medical illnessess of the patient.

Often patients taking multiple medications are elderly with physical handicaps such as arthritis, failing vision and memory, and lack of sophistication relative to the need for and shedule of taking these medications. Compliance with physician's instructions for taking these medications is poor, especially among the elderly on a multiple regime. Lack of compliance in taking medication as prescribed by the physician often results in a diminished effectiveness and occasionally adverse side effects. A common approach presently undertaken by patients to transport multiple medications is to gather up all the individual plastic pharmacy-dispensed variably labeled containers into small paper bags.

SUMMARY OF THE INVENTION

A general feature of the invention is that a plurality of receptacles for storing medication are flexibly interconnected for permitting the receptacles to be assembled in overlapping relationship to form a convenient package. Each receptacle includes a child resistant cap assembly that can be easily opened by a physically impaired patient and a storage area adjacent to the cap assembly for carrying indicia written in large letters designating instructions for taking medication stored in the receptacle.

Preferred embodiments of the invention include the following features. A pair of receptacles for storing medication are interconnected for permitting the receptacles to be assembled in an overlapping, polar position to form a convenient package. Each receptacle includes at least two relatively rigid storage units. Each storage unit includes a medication storage compartment having a child-resistant cap assembly and a smaller compartment contiguous with and adjacent to the medication storage compartment. The smaller compartment is capable of receiving a cap assembly of another receptacle when the receptacles are assembled in an overlapping relationship. The smaller compartment also includes an area for carrying indicia designating instructions for taking medication stored in the medication storage compartment. A flexible outer cover wraps and secures the receptacles together to form a convenient carrying package. The outer cover includes a transparent pocket for securing a card, which may list medications contained in the receptacles and the associated medical illnesses of a patient. The outer cover also provides a belt loop so that the capsule package can be fastened to a waist belt or shoulder strap.

In another aspect of the invention, the receptacle is a generally rectangular container formed with a circular opening. A label which allows indicia to be written with a grease pencil is fixed to a relatively rigid panel adjacent to the cap assembly.

The advantages of the invention are as follows. The capsule package provides a transport vehicle for the patient requiring medication while away from home. It also provides a means for identifying the nature of the medication and its schedule and the reasons for taking it. This information is of great value when the patient visits a physician in either a scheduled or emergency setting. The availability of this information also enhances the compliance of the patient to take the medication as prescribed by the physician by enhancing drug identification. Further, room is provided for instructions to be written large enough to aid an elderly person with poor eyesight.

DESCRIPTION OF THE PREFERRED EMBODIMENTS

The drawings are briefly described as follows.

Drawings

Structure

Figure 1:
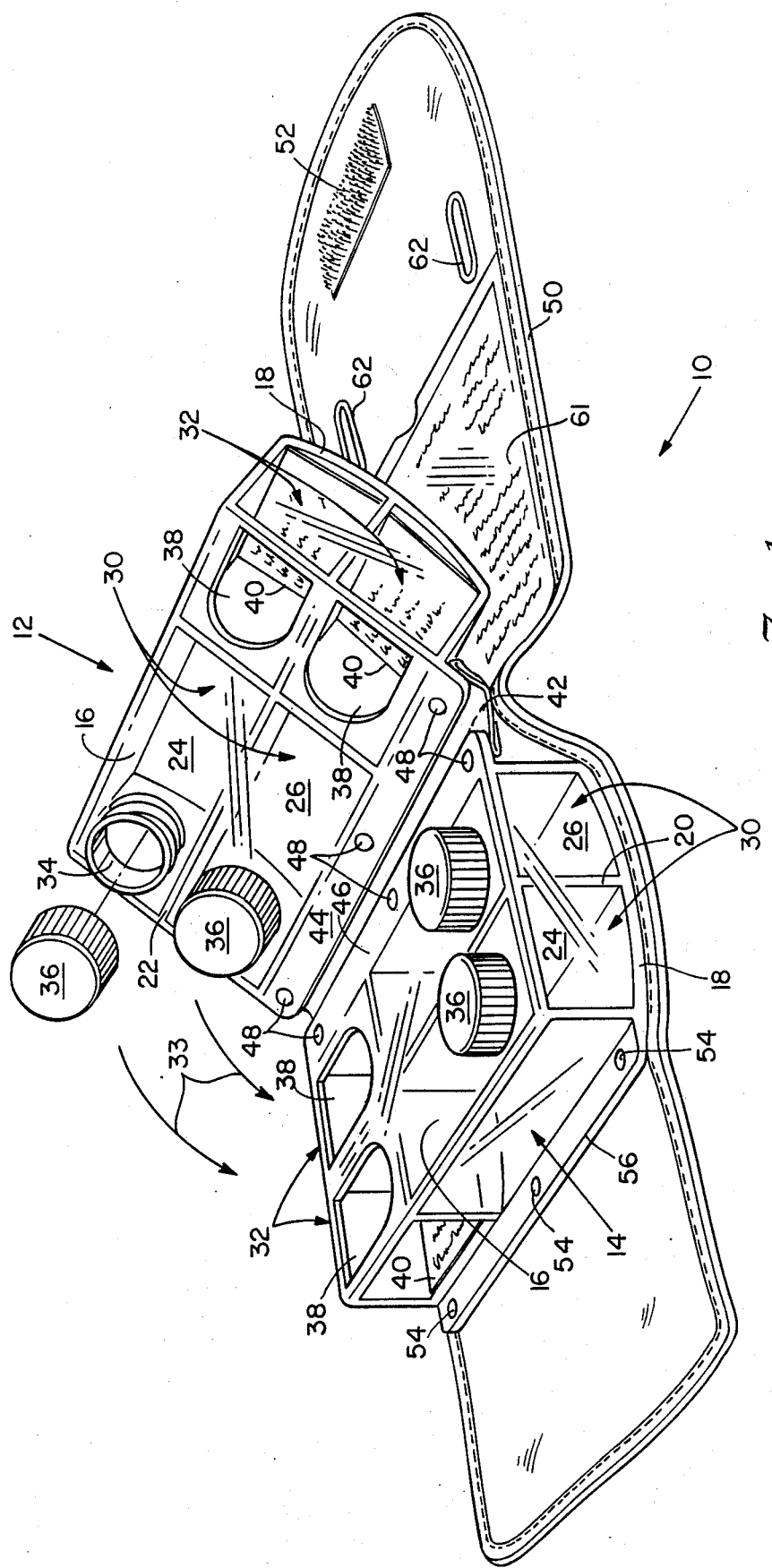
FIG. 1 is a perspective view of a capsule package assembly.

As shown in FIG. 1, two receptacles 12, and 14 for storing medication are flexibly connected for permitting the receptacles to be assembled in an overlapping relationship to form a convenient package. Each receptacle is generally rectangular and is approximately 5 inches long by 3 inches wide by ⅝ inch deep. Preferably both receptacles 12, 14 are made of transparent material such as rigid, durable plastic. A partition 20, 22 within each receptacle equally divides them into two storage units 24, 26. Each unit 26, 28 consists of a medication storage compartment 30 and a smaller, adjacent compartment 32. The medication storage compartment 30 includes an opening 34, approximately 1 inch in diameter, for accommodating a child proof screw on cap 36. The smaller compartment 32 has a semicircular opening 38, which permits a card 40 to be easily placed through the opening 38 and at the bottom of the compartment 32. It is preferred that card 40 is large enough to include instructions written in large letters for taking medication stored in the medication storage compartment 30.

As shown, the receptacles 12, 14 are hinged together by a flexible material 42 in polar opposition to each other. When the receptacles are folded together, caps of one receptacle fit into the smaller compartments 32 of the other receptacle as indicated by arrows 33. Flexible material 42, which may be made from cloth or soft plastic, is attached to flanges 44, 46 formed along the receptacles' top surface 16 by rivets 48. Alternately, flexible material 42 may be glued to the sides of the receptacles.

Figure 2:
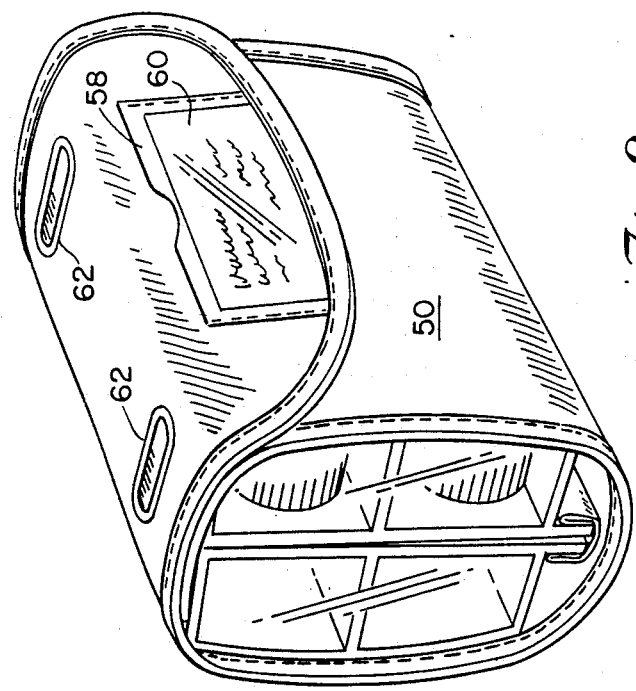
FIG. 2 is a perspective view of the capsule package folded over and stacked to form a convenient carrying package.

Referring also to FIG. 2, an outer cover 50 is used for wrapping the receptacles into a convenient carrying package. The outer cover 50 is preferably made of oft pile cloth and includes a patch of hook material 52 for fastening the ends of the cover together. The outer cover 50 is secured to the bottom receptacle 14 by rivets 54 along a bottom flange 56 and stitched to the hinge between the receptacles. The outer cover 50 includes a clear plastic envelope 58 on the exterior of the outer cover 50 for inserting a card 60 for displaying the name and address of a patient in large letters. A large clear plastic envelope 61 is also provided on the interior of the outer cover for placing and additional card, which may list the medications contained in the receptacles, the associated medical illnesses, and the name of the physician prescribing the medication.

Figure 3:
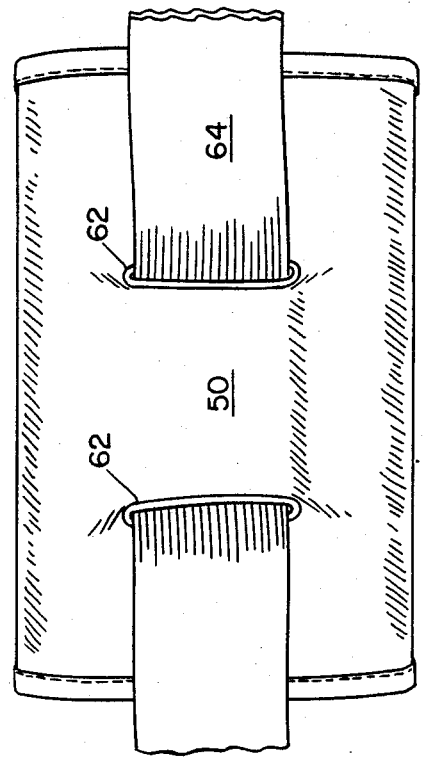
FIG. 3 is a view of the back side of the capsule package showing a belt looped through stitched slots for carrying the package.

The capsule package may be conveniently carried by a belt 64 or shoulder strap (not shown) fitted through slots 62 formed in the outer cover at the back of the package (FIG. 3) or at the top of the package (FIG. 2).

Figure 4:
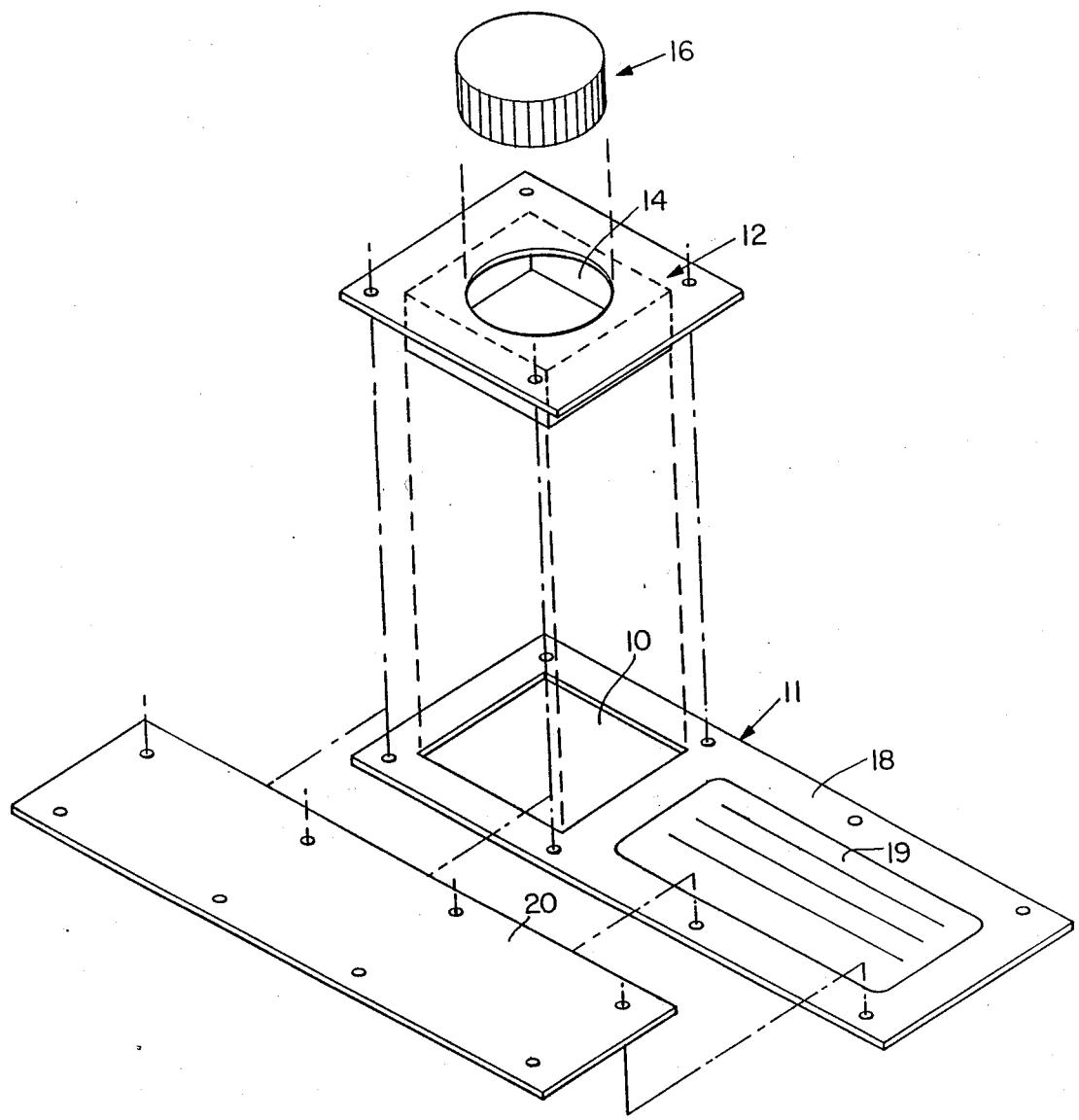
FIG. 4 is an exploded perspective view of a single container, assembly.

In another embodiment, a plurality of adjacent receptacles are interconnected together by flexible material for permitting the receptacles to be assembled in overlapping relationship to form a convenient package. Referring to FIG. 4, a single plastic container assembly includes a rectangular opening 10 in a main assembly piece 11 which accomodates a generally rectangular container 12 formed with a circular opening 14 at the top. Typically container 12 is approximately 1 ½ inches wide, 2 inches long and ⅜ inch deep. A child-resistant cap assembly 16, large enough so that a physically impaired elderly person may easily open it, selectively covers the opening 14.

Adjacent to container 12 is a relatively rigid panel 18. Panel 18 is large enough to carry instructions in large letters inscribed with a grease pencil or other suitable marker so that the instructions may be easily read by an elderly person with poor eyesight. Alternatively, a medical information label 19 may be placed on the panel for carrying in large letters the dosage instructions, such as the number of pills to be taken and the times of taking each dosage. A flexible connection piece 20 made from plastic or other suitable material is connected to a long edge of the main assembly piece 11. Connection may be made by press fitting plastic pop rivets (not shown) into adjacent holes. Alternately, the adjacent units may be detachably secured by pressure sensitive adhesives or other suitable means to allow assembly of any number of receptacles.

An advantage of displaying instructions with indicia or a label secured to the panel by a peelable adhesive or other means for detachably securing the label is that the receptacles may be refilled with different medicaitons accompanied by different instructions. Yet, the invention is relatively inexpensive so that the receptacles may be disposable.

Figure 5:
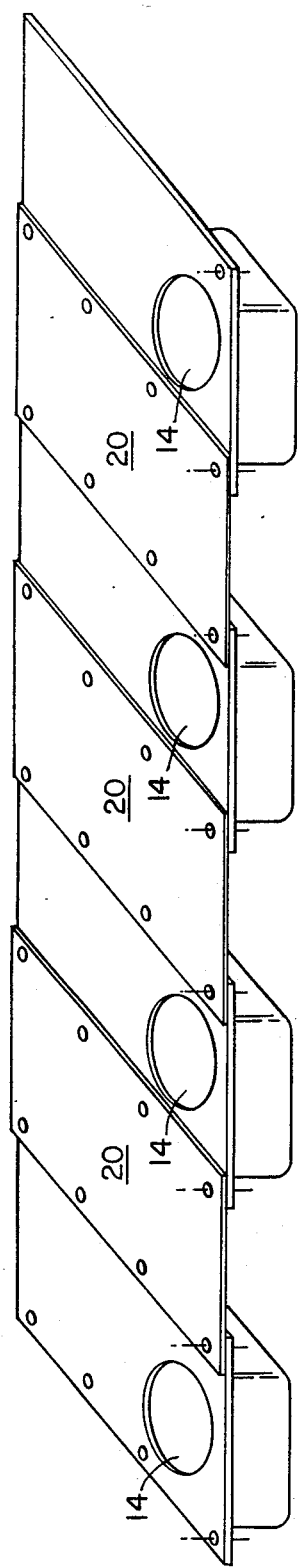
FIG. 5 is a perspective view of four container assemblies interconnected by flexible connecting pieces.
Figure 6:
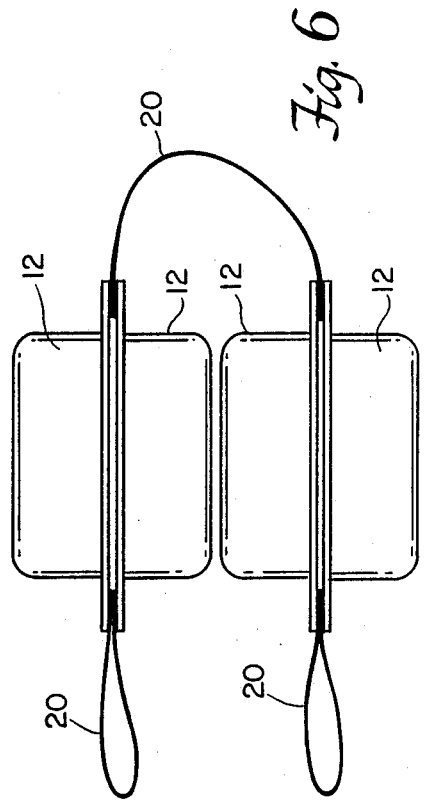
FIG. 6 is a side view of four container assemblies stacked.

Referring to FIG. 5 four container assemblies with openings 14 are interconnected by flexible container pieces 80. The adjacent container assemblies are arranged so that the label of one medication container is clearly separated from another. The four containers may be then folded over accordian style and stacked so as to form a convenient carrying package as shown in FIG. 6.

Other embodiments are within the following claims.

I claim:
1. A medication container comprising,
receptacles, each receptacle formed with a coverable opening adjacent an area for carrying large indicia readable by a person with relatively poor eyesight designating instructions for taking medication stored in said receptacle on a relatively rigid panel secured to said receptacle adjacent to said opening;
a child-resistant cap assembly for each receptacle that is easily opened by a patient with malfunctioning fingers for selectively closing said coverable opening; and
flexible material for interconnecting adjacent ones of said receptacles for permitting the interconnected receptacles to be assembled in overlapping relationship to form a convenient package.

2. The medication container of claim 1 wherein said container comprises two receptacles connected in polar opposition.

3. The medication container of claim 2 wherein each receptacle is a generally rigid rectangular container having a first compartment for storing medication and a second compartment for receiving a cap assembly of another receptacle when the connected receptacles are assembled in said overlapping relationship.

4. The medication container of claim 1 wherein each receptacle comprises a generally rectangular container having a first compartment for storing medication and a second compartment for carrying said indicia for taking medication stored in said first compartment.

5. The medication container of claim 1 wherein each receptacle comprises a partition separating each of said plurality of receptacles into two storage units, each unit having a first compartment for storing medication and a second compartment for receiving a cap assembly of another receptacle when the receptacles are assembled in said overlapping relationship to form a convenient carrying package.

6. The medication container of claim 5 wherein said second compartment has an area for carrying large indicia designating instructions for taking medication stored in said first compartment.

7. The medication container of claim 1 further comprising a flexible outer cover for wrapping and securing said receptacles in said overlapping relationship.

8. The medication container of claim 7 wherein said flexible cover further comprises a transparent pocket for securing a card listing medications contained in said receptacles and the associated medical illnesses of a patient.

9. The medication container of claim 8 wherein said flexible cover further comprises a second transparent pocket for securing a card listing the name of the patient, his address, and the name of his physician prescribing medication.

10. The medication container of claim 7 wherein ends of said flexible outer cover are secured together by a hook and pile fastener.

11. The medication container of claim 7 further comprising a belt loop formed in said flexible outer cover for allowing a patient to attach the medication container to a waist belt or shoulder strap.

12. The medication container of claim 1 wherein each receptacle is comprises of rigid plastic and is 5 inches long by 3 inches wide and ⅜ of an inch deep.

13. The medication container of claim 1 wherein each receptacle is made from transparent material.

14. A medication container of claim 1 wherein said receptacle is a generally rectangular container formed with a circular opening.

15. A medication container of claim 1 further comprising a label fixed to said panel for allowing indicia to be written with a marker.

16. A medication container of claim 14 wherein the receptacles are detachable.

17. A medication container of claim 1 wherein each receptacle is approximately 1 ½ inches, 2 inches long and ⅝ inches deep.

18. A medication container of claim 1 wherein the area of said panel is greater than that of the cross sectional area of said receptacle perpendicular to the axis of said opening.

19. A medication container of claim 18 wherein said panel is perpendicular to the axis of said opening.

20. A medication container of claim 1 wherein said panel is perpendicular to the axis of said opening.

* * * * *